US012635873B2

(12) United States Patent
Boutinon et al.

(10) Patent No.: US 12,635,873 B2
(45) Date of Patent: May 26, 2026

(54) METHOD, SYSTEM AND COMPUTER-PROGRAM FOR ESTIMATING REFRACTION OF AN EYE OF AN INDIVIDUAL

(71) Applicant: Essilor International, Charenton-le-Pont (FR)

(72) Inventors: Stéphane Boutinon, Paris (FR); Marius Peloux, Palaiseau (FR); Philippe Pinault, Nogent sur Marne (FR)

(73) Assignee: Essilor International, Charenton-le-Pont (FR)

( * ) Notice: Subject to any disclaimer, the term of this patent is extended or adjusted under 35 U.S.C. 154(b) by 291 days.

(21) Appl. No.: 18/554,355

(22) PCT Filed: Apr. 13, 2022

(86) PCT No.: PCT/EP2022/059966
§ 371 (c)(1),
(2) Date: Oct. 6, 2023

(87) PCT Pub. No.: WO2022/219095
PCT Pub. Date: Oct. 20, 2022

(65) Prior Publication Data
US 2024/0225441 A1 Jul. 11, 2024

(30) Foreign Application Priority Data

Apr. 16, 2021 (EP) ..................................... 21305503

(51) Int. Cl.
A61B 3/103 (2006.01)
A61B 3/00 (2006.01)
A61B 3/14 (2006.01)

(52) U.S. Cl.
CPC ............ *A61B 3/103* (2013.01); *A61B 3/0025* (2013.01); *A61B 3/14* (2013.01)

(58) Field of Classification Search
CPC ......... A61B 3/103; A61B 3/0025; A61B 3/14; A61B 3/0008; A61B 3/04; A61B 3/111; A61B 3/112; A61B 3/113; A61B 3/152
(Continued)

(56) References Cited

U.S. PATENT DOCUMENTS 8,824,779 B1 9/2014 Smyth
10,531,794 B1 1/2020 Reis et al.
(Continued)

FOREIGN PATENT DOCUMENTS

EP 3 669 751 A1 6/2020
JP 2014-526312 A 10/2014
(Continued)

OTHER PUBLICATIONS

International Search Report mailed on Jul. 14, 2022 in PCT/EP2022/059966 filed on Apr. 13, 2022 (4 pages).
(Continued)

*Primary Examiner* — Mohammed A Hasan
(74) *Attorney, Agent, or Firm* — Oblon, McClelland, Maier & Neustadt, L.L.P.

(57) ABSTRACT

A method for estimating refraction of an eye of an individual, including: a) providing a set of N acquired eccentric photorefraction images of the eye, b) setting values for a set of parameters including at least sphere, c) providing a set of N simulated eccentric photorefraction images, d) determining an estimator of a difference between the set of N acquired eccentric photorefraction images and the set of N simulated eccentric photorefraction images, e) performing an optimization using an optimization algorithm so as to optimize the estimator by adjusting values for the set of
(Continued)

parameters and iterating steps c) and d), and f) deducing an estimation of at least one refraction parameter of the eye.

19 Claims, 6 Drawing Sheets

(58) Field of Classification Search
USPC ......................................................... 351/205
See application file for complete search history.

(56) References Cited

U.S. PATENT DOCUMENTS

| | | | | |
|---|---|---|---|---|
| 11,617,508 | B2 * | 4/2023 | Sharma .................. | A61B 3/005 348/78 |
| 2004/0054358 | A1 * | 3/2004 | Cox .................... | A61F 9/00806 606/5 |
| 2005/0007551 | A1 * | 1/2005 | Wakil .................. | A61B 3/1015 351/205 |
| 2009/0015787 | A1 * | 1/2009 | Guillen ................ | A61B 3/1015 351/205 |
| 2019/0117060 | A1 | 4/2019 | Hegde et al. | |
| 2019/0167093 | A1 | 6/2019 | Breuninger et al. | |
| 2022/0039649 | A1 | 2/2022 | Escalier et al. | |
| 2022/0361745 | A1 * | 11/2022 | De Rossi ................. | A61B 3/14 |

FOREIGN PATENT DOCUMENTS

| | | |
|---|---|---|
| WO | WO 2017/182856 A1 | 10/2017 |
| WO | WO 2018/100589 A1 | 6/2018 |

OTHER PUBLICATIONS

Ying-Ling Chen et al: "Simulation of eccentric photorefraction images", Optics Express, vol. 11, No. 14, Jul. 14, 2003 (Jul. 14, 2003), pp. 1628-1642, XP055401022.

Wesemann et al; "Theory of eccentric photorefraction (photoretinoscopy): astigmatic eyes", J. Opt. Soc. Am. A/vol. 8, No. 12/Dec. 1991, pp. 2038-2047.

Kusel et al; "Light-intensity distribution in eccentric photorefraction crescents", J. Opt. Soc. Am. A/vol. 15, No. 6/Jun. 1998, pp. 1500-1511.

Gekeler F., et al.; "Measurement of Astigmatism by Automated Infrared Photoretinoscopy", vol. 74 No. 7, Jul. 1997, pp. 472-482.

Roorda et al.; "Geometrical theory to predict eccentric photorefraction intensity profiles in the human eye", vol. 12, No. 8/Aug. 1995/J. Opt. Soc. Am. A, pp. 1647-1656.

Japanese Office Action issued Nov. 11, 2024, in corresponding Japanese Patent Application No. 2023-563035 (with English Translation), 8 pages.

\* cited by examiner

METHOD, SYSTEM AND COMPUTER-PROGRAM FOR ESTIMATING REFRACTION OF AN EYE OF AN INDIVIDUAL

TECHNICAL FIELD OF THE INVENTION

The invention relates to a method and a system for evaluating refraction of an eye of an individual.

More precisely the invention relates to a method and a system for estimating refraction of an eye of an individual. The invention also relates to a computer-program for estimating refraction of an eye of an individual. The method, system and/or and computer-program may be used for determining a prescription for ophthalmic lenses adapted for the individual or for manufacturing an ophthalmic lens according to the estimated refraction. The invention also provides refraction measurements that may be used as a starting point for further subjective refraction performed with another device.

BACKGROUND INFORMATION AND PRIOR ART

Numerous documents describe devices and methods for measuring refraction of the eye of an individual. Subjective refraction methods are based on interactions with the individual viewing different optotypes and using a set of lenses with various refraction corrections. Objective refraction methods are based on measurements of the optical properties of the eye considered. In particular, some methods and devices for measuring objective refraction are based on eccentric photorefraction or photoretinoscopy.

Eccentric photorefraction is used to perform objective refraction by illuminating the user's eye using an eccentric light source and observing the image of the pupil with a camera. In most cases, reflected light forms on the pupil in the detected image, a light shape with a complementary, non luminous shape, called dark crescent. The analysis of the size, shape and orientation of the bright or dark crescent enables to estimate refraction of the eye depending on the position of the eccentric light source. For example, the publications W. Wesemann, A. M. Norcia, D. Allen "Theory of eccentric photo refraction (photoretinoscopy): astigmatic eyes", J. Opt. Soc. Am. A, Vol. 8, No. 12, 1991, pages 2038-2047 or R. Kusel, U. Oechsner, W. Wesemann, S. Russlies, E. M. Irmer, and B. Rassow, "Light-intensity distribution in eccentric photorefraction crescents," J. Opt. Soc. Am. A 15, 1500-1511 (1998) disclose analytic expressions for the bright part. A rather simple method to deduce sphere, cylinder and axis values from measurements of a light gradient along three meridians is described in Gekeler F, Schaeffel F, Howland H C, Wattam-Bell J, "Measurement of astigmatism by automated infrared photoretinoscopy", Optometry and Vision Science: Official Publication of the American Academy of Optometry, 1997, July; 74(7):472-482. DOI: 10.1097/00006324-199707000-00013.

However, these methods do not take into account higher order aberrations of the eye. Moreover, these publications are mostly theoretical, but do not disclose methods and systems enabling to obtain quickly refraction measurements. Also, depending on the user ametropia, it may be difficult to detect the crescent.

In developed countries, professional optometrists generally use auto-refractometers. However, these systems are expensive and cumbersome.

There is a need for a system and method providing an estimation of photorefraction that is quick, small, easy-to-use and at low cost.

SUMMARY OF THE INVENTION

Therefore one object of the invention is to provide a method for estimating refraction of an eye of an individual, the method comprising the following steps:

a) Providing a set of N acquired eccentric photorefraction images of the eye, where N is an integer higher than or equal to one;

b) Initializing values for a set of parameters including at least sphere;

c) Providing a set of N simulated eccentric photorefraction images using a simulation model according to the values of the set of parameters;

d) Determining an estimator of a difference between the set of N acquired eccentric photorefraction images and the set of N simulated eccentric photorefraction images;

e) Performing an optimization using an optimization algorithm so as to optimize said estimator by adjusting values for the set of parameters and iterating steps c) and d), and f) Deducing an estimation of at least one refraction parameter of the eye from the adjusted values for the set of parameters.

According to a particular and advantageous embodiment, step a) includes the following steps g) to i), and each step c) includes the following step j):

g) placing a system comprising an image capturing device having an aperture and a plurality of M light sources in front of the eye, where M is an integer higher than or equal to two, the plurality of M light sources being arranged eccentrically around the aperture of the image capturing device at determined positions along at least two directions transverse to an optical axis of the image capturing device, each light source of the M light sources being adapted and configured to illuminate the eye with a light pulse;

h) illuminating the eye using each light source of the plurality of M light sources;

i) recording the set of N acquired eccentric photorefraction images of the eye using the image capturing device, where N is lower than or equal to M, each image of the set of N acquired eccentric photorefraction images representing the eye illuminated by the light pulse of at least one light source of the plurality of M light sources;

j) generating the set of N simulated eccentric photorefraction images using the simulation model according to the values of the set of parameters.

According to a particular and advantageous aspect of this method, the step b) comprises selecting a set of three acquired eccentric photorefraction images from the set of N acquired eccentric photorefraction images, the set of three acquired eccentric photorefraction images being recorded using three light sources arranged along three directions transverse to the optical axis of the image capturing device; processing each of the three acquired eccentric photorefraction images so as to determine a dark crescent size and tilt angle, and deducing therefrom three ophthalmic power values for the three directions.

According to an embodiment, M is equal to N and the step h) comprises illuminating the eye using sequentially each light source of the plurality of M light sources and the step i) comprises acquiring each image of the set of N eccentric photorefraction images when the eye is illuminated by the light pulse of one light source of the plurality of M light sources.

According to another embodiment, N is lower than M and the step h) comprises a step of illuminating the eye using simultaneously with two light sources of the plurality of M light sources and the step i) comprises a step of acquiring one image of the set of N eccentric photorefraction images when the eye is illuminated by the light pulse of two light sources.

Advantageously, said simulation model is based on a geometrical-optical model of light intensity distribution or on a ray-tracing model.

According to a particular aspect, the simulation model further depends on hardware parameters such as power of each light source, on ophthalmic parameters such as corneal reflection and/or on operational parameters such as position of the image capturing device relatively to the eye.

According to another particular aspect, the estimator is based on pixel-by-pixel difference between the set of N acquired eccentric photorefraction images and the set of N simulated eccentric photorefraction images, or the estimator is based on comparing a preprocessed set of N acquired eccentric photorefraction images and a preprocessed set of N simulated eccentric photorefraction images.

Advantageously, the optimization algorithm or the minimization algorithm is based on a method without gradient computation, such as simplex or Nelder-Mead, or on a method with gradient computation, such as Levenberg-Marquardt.

According to an embodiment, the method further comprises determining a distance between the image capturing device and the eye and/or an orientation of the image capturing device relatively to the eye.

According to a particular and advantageous aspect, the set of parameters further comprises at least one other parameter of the eye among: cylinder, axis, pupil diameter, higher order aberrations, half interpupillary distance, direction of gaze, amount of red reflex, and Stiles-Crawford parameter.

According to a particular aspect, the method is performed at a first distance and at a second distance between the image capturing device and the eye.

Preferably, the plurality of M light sources comprises 3, 6, 9 or 12 light sources.

Advantageously, the plurality of M light sources comprises light emitting diodes.

A further object of the invention is to provide a system for estimating refraction of an eye of an individual, the system being adapted to communicate with a mobile device or with a remote computer.

The above objects are achieved according to the invention by providing a system comprising an image capturing device and a plurality of M light sources, where M is an integer higher than or equal to two, the plurality of M light sources being arranged eccentrically around the image capturing device at determined positions along at least two directions transverse to an optical axis of the image capturing device; the system being adapted and configured to illuminate the eye with a light pulse using each light source of the plurality of M light sources; the image capturing device being configured to record a set of N acquired eccentric photorefraction images of the eye, where N is an integer lower than or equal to M, each image of the set of N acquired eccentric photorefraction images representing the eye illuminated by the light pulse of at least one light source of the plurality of M light sources; the system comprising a calculation module comprising a memory and a processor arranged to execute a program instructions stored in the memory to:

k) initialize values for a set of parameters including at least sphere;

l) generate a set of N simulated eccentric photorefraction images using a simulation model based on the values of the set of parameters;

m) calculate an estimator of a difference between the set of N acquired eccentric photorefraction images and the set of N simulated eccentric photorefraction images;

n) use a minimization algorithm so as to minimize said estimator by adjusting values for the set of parameters and iterating steps l) and m); and o) deduce an estimation of at least one refraction parameter of the eye from the adjusted values for the set of parameters.

Advantageously, the image capturing device and the plurality of M light sources are mounted on an accessory removably attached to the mobile device.

According to an embodiment, the calculation module is included in the accessory.

According to another embodiment, the calculation module is included in the mobile device or in the remote computer.

A further object of the invention is to provide a computer-program product comprising one or more stored sequences of instructions that are accessible to a processor, and which, when executed by the processor, causes the processor to carry out at least the following steps to:

p) provide a set of N acquired eccentric photorefraction images, wherein each image of the set of N acquired eccentric photorefraction images represents an eye illuminated by a light pulse of at least one light source of a plurality of M light sources arranged eccentrically around an image capturing device at determined positions along at least two directions transverse to an optical axis of the image capturing device, where M is an integer higher than or equal to two, and N is an integer lower than or equal to M;

q) initialize values for a set of parameters including at least sphere;

r) generate a set of N simulated eccentric photorefraction images using a simulation model based on the values of the set of parameters;

s) calculate an estimator of a difference between the set of N acquired eccentric photorefraction images and the set of N simulated eccentric photorefraction images;

t) use an optimization algorithm so as to optimize said estimator by adjusting values for the set of parameters and iterating steps r) and s); and u) deduce an estimation of at least one refraction parameter of the eye from the adjusted values for the set of parameters.

DETAILED DESCRIPTION OF EXAMPLE(S)

The following description with reference to the accompanying drawings will make it clear what the invention consists of and how it can be achieved. The invention is not limited to the embodiment/s illustrated in the drawings. Accordingly, it should be understood that where features mentioned in the claims are followed by reference signs, such signs are included solely for the purpose of enhancing the intelligibility of the claims and are in no way limiting on the scope of the claims. For a more complete understanding of the description provided herein and the advantages thereof, reference is now made to the brief descriptions below, taken in connection with the accompanying drawings and detailed description, wherein like reference numerals represent like parts. In the accompanying drawings:

FIG. 1A, respectively 1B, shows a perspective view of a system for estimating refraction of an eye of an individual according to a first, respectively second, embodiment;

Figure 5:
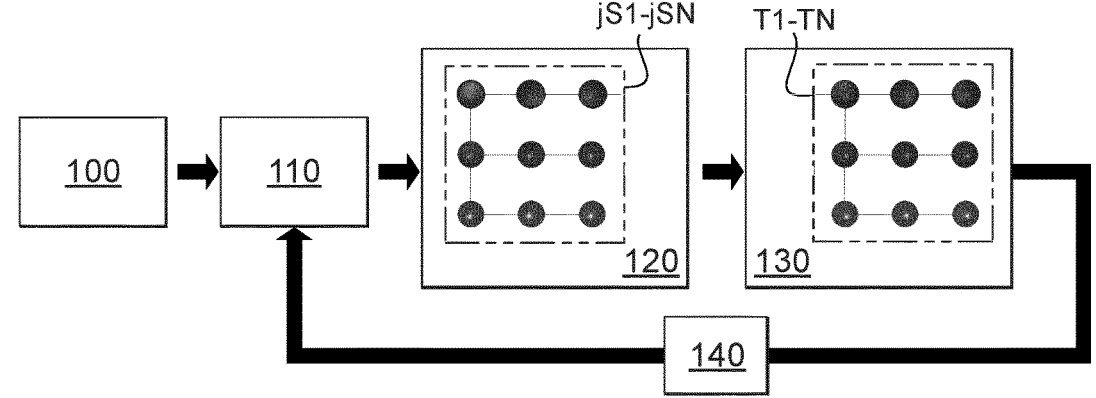
Figure 6:
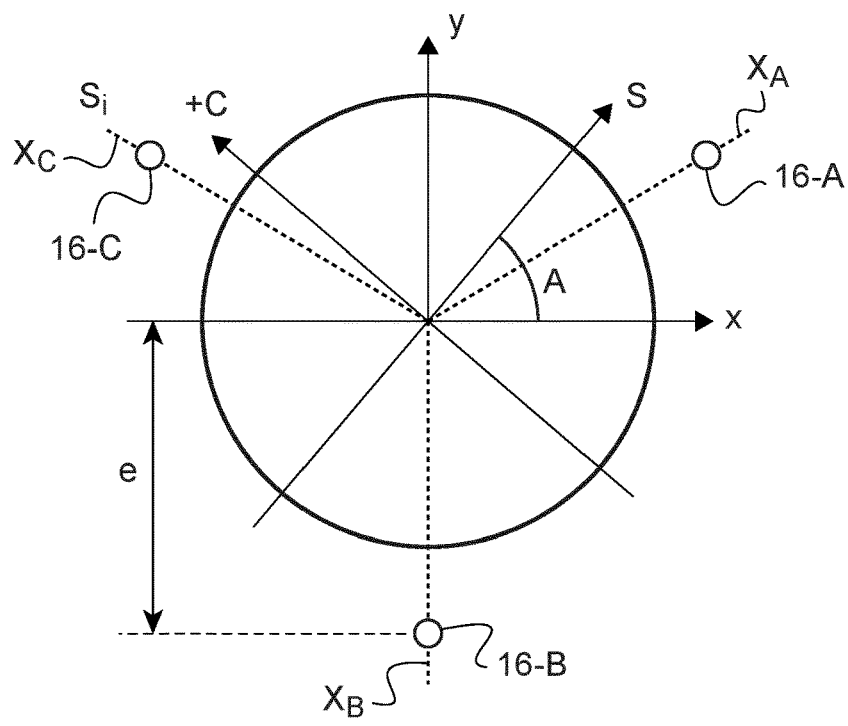
Figure 7:
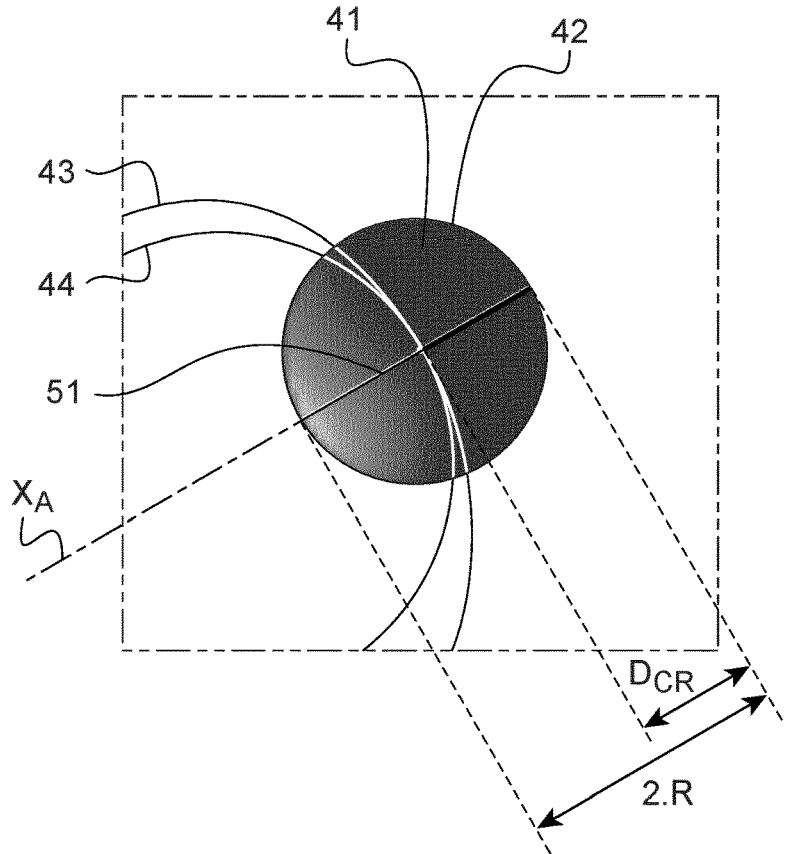
Figure 8:
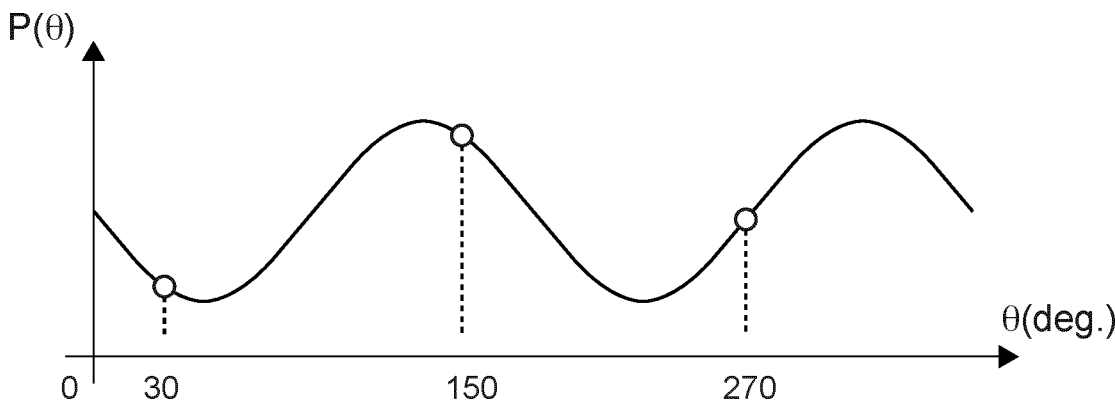
Figure 9:
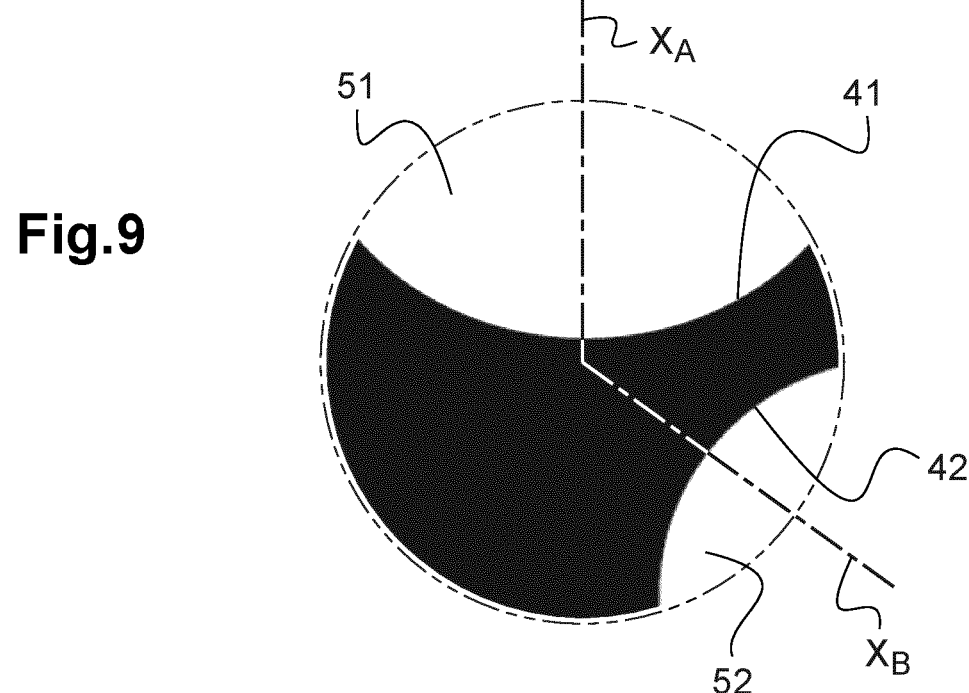
Figure 10:
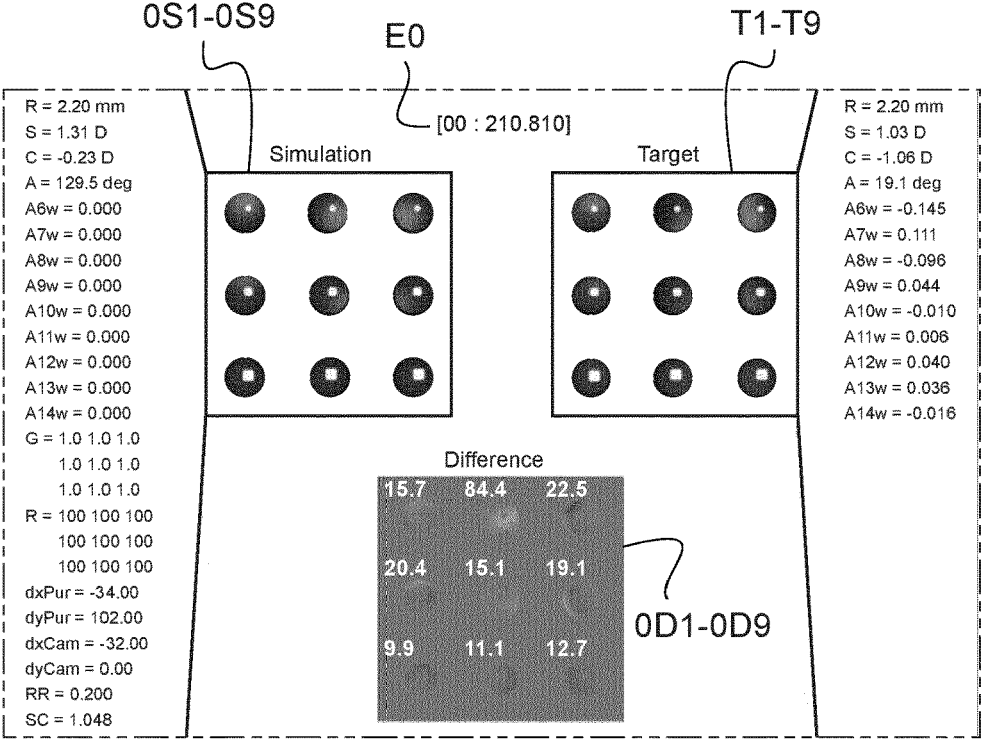
Figure 11:
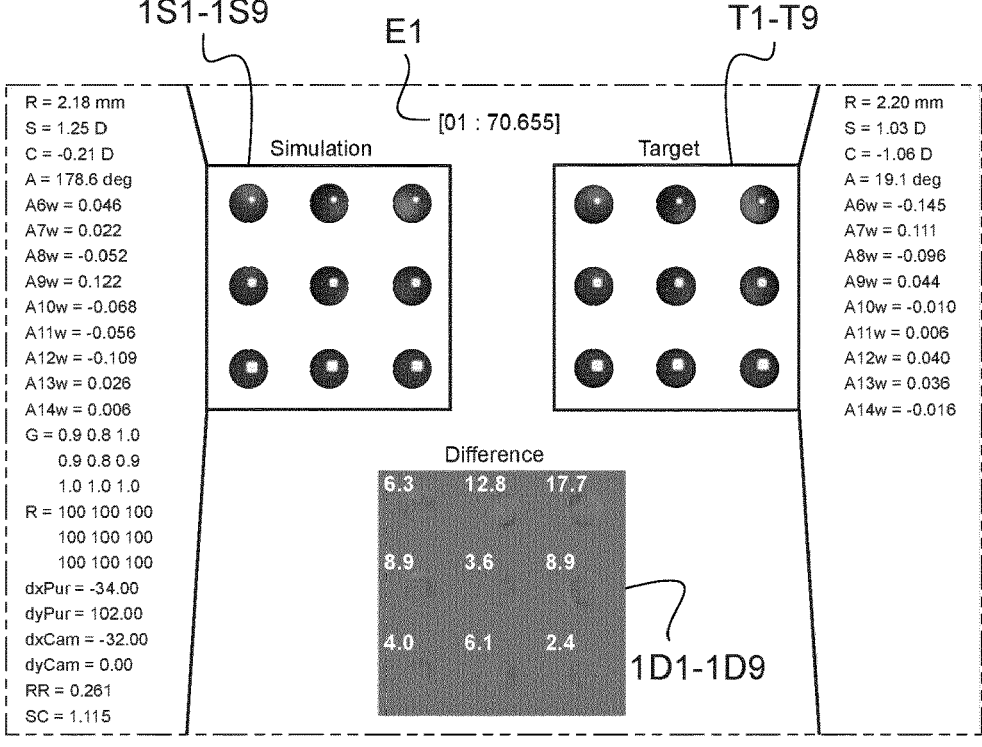
Figure 12:
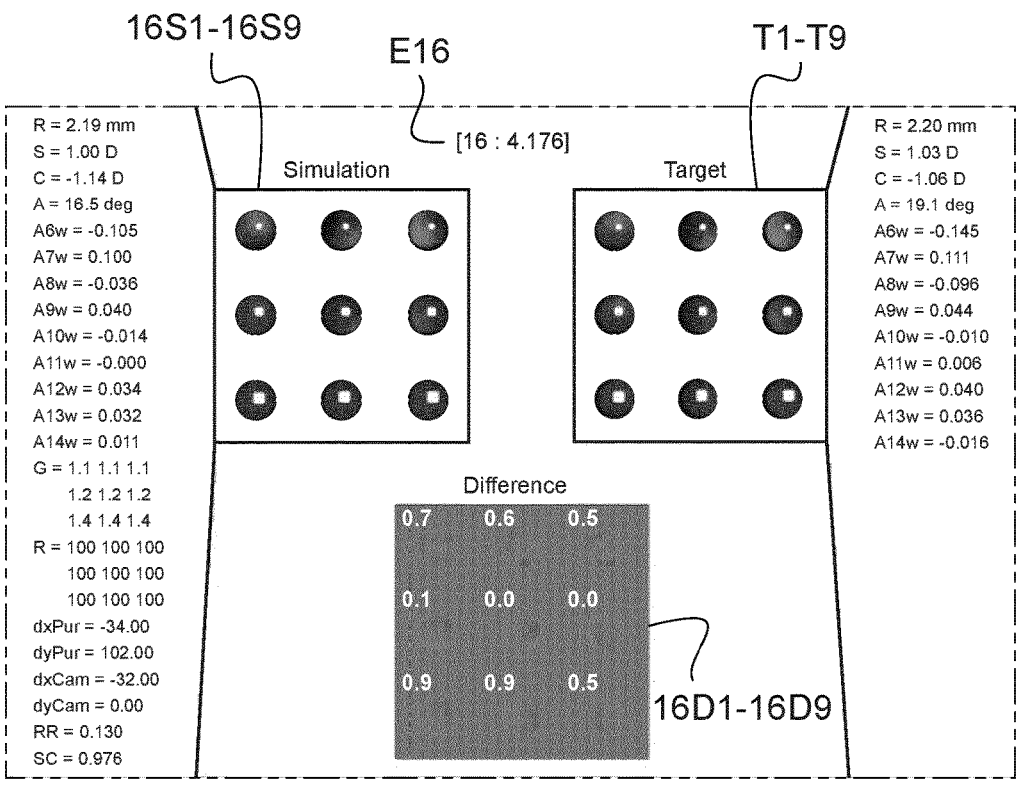

FIG. 5 schematically represents a flow chart of a method for estimating refraction of an eye of an individual according to the invention;

FIG. 6 represents schematically an arrangement of three light sources placed at a same distance from the camera on three distinct meridians;

FIG. 7 illustrates an example of acquired eccentric photorefraction image with a dark crescent obtained using one light sources along one meridian;

FIG. 8 schematically represents a method for determining initial values of sphere, cylinder and axis based on eccentric photorefraction images using three light sources along three distinct meridians;

FIG. 9 schematically represents an example of acquired eccentric photorefraction image using simultaneously two light sources along two distinct meridians;

FIG. 10 shows an initial set of N simulated eccentric photorefraction images at an initial step of the method based on initial values of parameters, and an initial estimator value of the comparison with a set of 9 acquired eccentric photorefraction images;

FIG. 11 shows intermediate results after one iteration, with another set of N simulated eccentric photorefraction images compared to the same set of 9 acquired eccentric photorefraction image as on FIG. 10, and the corresponding values of estimator and parameters resulting from this simulation;

FIG. 12 shows the final results after 16 iterations with a final set of 9 simulated eccentric photorefraction images compared to the same set of 9 acquired photorefraction images, and the final values of estimator and parameters resulting from the minimization between the two sets of images.

In the description which follows the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may be embodied in a wide variety of contexts. Embodiments discussed herein are merely representative and do not limit the scope of the invention. It will also be obvious to one skilled in the art that all the technical features that are defined relative to a process can be transposed, individually or in combination, to a device and conversely, all the technical features relative to a device can be transposed, individually or in combination, to a process.

Device and Method

Figure 1A:
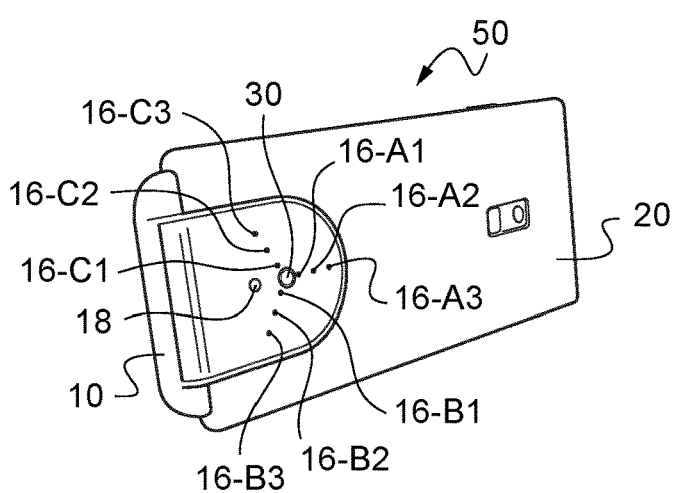
Figure 1B:
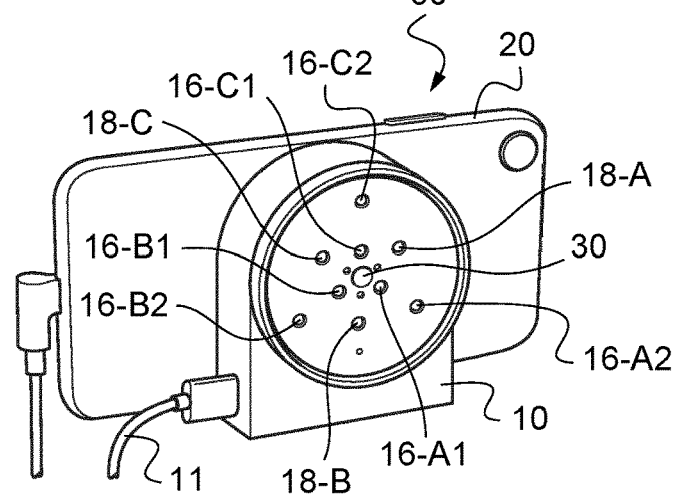

FIGS. 1A and 1B represent a system 50 for estimating refraction of an eye 2 of a subject 1. The system 50 comprises a photorefraction module 10, or add-on, linked to a mobile device 20 such as a smartphone, a tablet personal computer or a laptop computer. Advantageously, the photorefraction module 10 is mechanically fastened to the mobile device 20.

The photorefraction module 10 is connected to the mobile device 20 using a direct plug and socket connection as illustrated on FIG. 1A or using a wire connection 11 as illustrated on FIG. 1B. The photorefraction module 10 is configured to communicate with the mobile device 20 either using a wired connection or a wireless connection.

Figure 2:
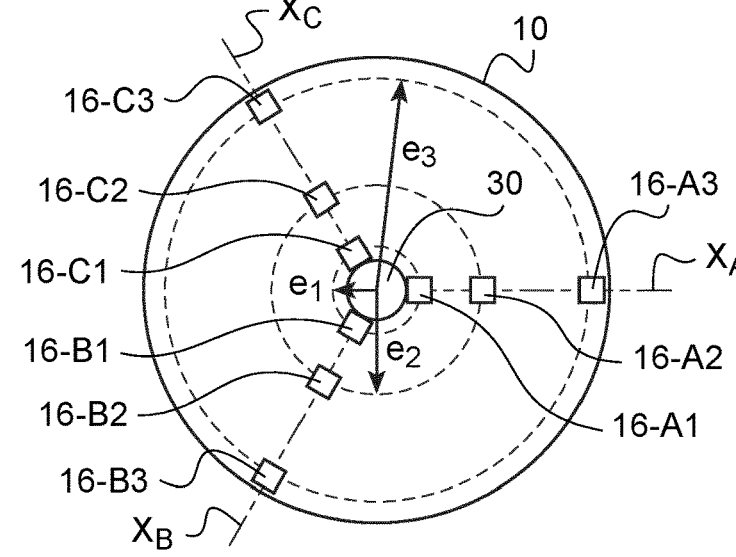
FIG. 2 is a front view of a photorefraction module comprising a camera and a plurality of light sources for estimating refraction of an eye of an individual according to an embodiment of the invention.

The photorefraction module 10 illustrated on FIGS. 1A, 1B and 2 comprises a camera 30 and a plurality of M light sources, wherein M is an integer higher than or equal to two. In other words, the minimum configuration comprises at least two light sources, 16-A and 16-B, arranged along two distinct meridians, $X_A$ and $X_B$.

For example on FIG. 2, the photorefraction module 10 comprises nine light sources 16-A1, 16-A2, 16-A3, 16-B1, 16-B2, 16-B3, 16-C1, 16-C2 and 16-C3. The three light sources 16-A1, 16-A2, 16-A3 are arranged along a same direction, or meridian $X_A$, transverse to the optical axis of the camera 30. Similarly, the three light sources 16-B1, 16-B2, 16-B3, respectively 16-C1, 16-C2, 16-C3, are arranged along another direction, or meridian $X_B$, respectively meridian $X_C$, both meridians $X_B$ and $X_C$ being transverse to the optical axis of the camera 30. The three meridians $X_A$, $X_B$ and $X_C$ correspond to three distinct directions in a same plane perpendicular to the optical axis of the camera 30. For example the three meridians $X_A$, $X_B$ and $X_C$ are separated by an angle of 120 degrees from each other.

As an option, the photorefraction module 10 further comprises another light source 18 (see FIG. 1A). Alternatively, the photorefraction module 10 further comprises another set of three light sources 18A, 18B, 18C arranged at another eccentricity and placed on three other meridians, as illustrated on FIG. 1B. According to another alternative, the photorefraction module 10 further comprises another set of three light sources 18A, 18B, 18C arranged on another and same meridian and placed at three different eccentricities from the camera.

In an example, the set i of light sources 16-Ai, 16-Bi, 16-Ci emits light at a first wavelength and the set of at least another light source 18, respectively 18A, 18B, 18C, emits light at a second wavelength, distinct from the a first wavelength. Generally, the first wavelength is in the near infrared or infrared range, for example around 850 nm, so that the pupil of the user remains unchanged when the light source is lit up.

The position of each light source 16, 18 relatively to the camera 30 is predetermined and fixed. Each set i of light sources 16-Ai, 16-Bi, 16-Ci is placed at a same distance, or eccentricity $e_i$, from the optical axis of the camera 30. The range of eccentricity is generally comprised between 0 and 20 mm. Advantageously, the range of eccentricity is generally comprised between 0.5 mm to 20 mm.

Advantageously, the light sources consist of light emitting diodes or leds. For example, the photorefraction module 10 comprises nine leds arranged at three different eccentricities along three different meridians. The camera 30 is adapted and configured for capturing eccentric photorefraction images of the eye 2 of the individual for each light source 16-Ai, 16-Bi, 16-Ci for i=1, 2, 3 that is lit successively. This configuration enables to acquire a set of N=9 eccentric photorefraction images per measurement.

In another example, the photorefraction module 10 comprises twelve light sources arranged along three meridians and at four different eccentricities.

Figure 3:
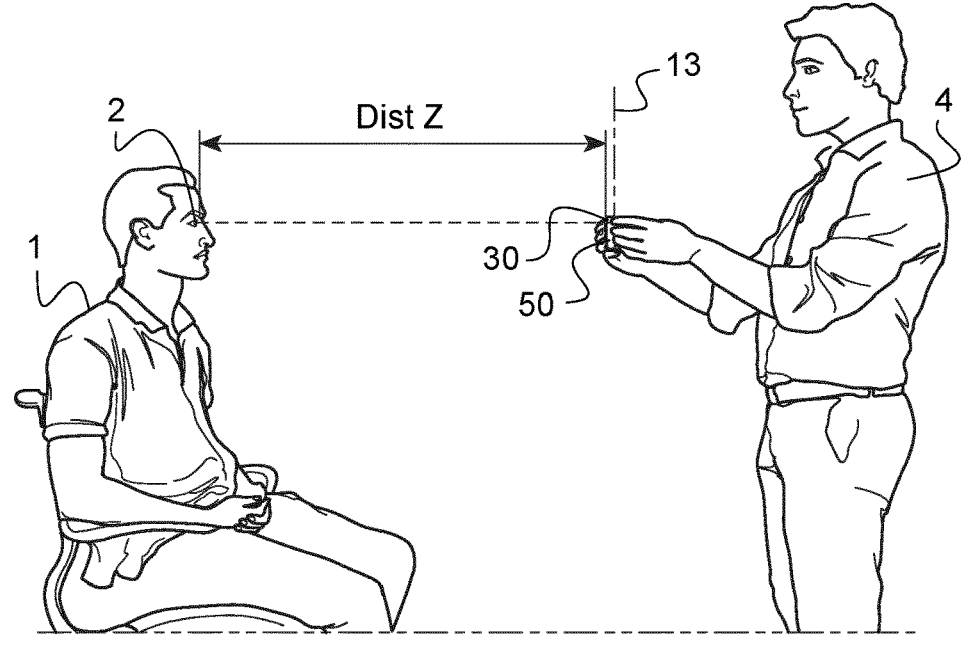
FIG. 3 shows an exemplary configuration to acquire a set of eccentric photorefraction images of at least one eye of a subject.

FIG. 3 shows a configuration for estimating refraction of an eye 2 of an individual using a system 50 according to the invention. An optometrist 4 or a technician holds the system 50 and arranges the position and direction of the optical axis of the camera 30 so as to be at the height of the face of the individual and so that the plane of the light sources 16, 18 is vertical. The photorefraction module 10 is at a distance DistZ from the eye 2 of the individual. Generally, the distance DistZ is about 1 meter, and can be comprised between 30 cm and 2 m. In an example, we consider two distance measurement values: 1 m and 0.5 m. Thus, in case the measurement at 1 m returns no accurate result, the measurement is performed at the distance of 50 cm. Advantageously, the system 50 comprises means for measuring the distance DistZ, such as an autofocus device. Alternatively, the subject 1 holds the system 50 and looks at the camera directly or by reflection on a mirror surface and takes the pictures himself for self-refraction measurement. The system 50 is very tolerant in positioning and non-invasive.

The system 50 also comprises a calculation module comprising a memory and a processor, arranged to execute a program instructions stored in the memory to implement a method for estimating refraction of an eye of an individual according to the invention. The calculation module is placed inside the photorefraction module 10 or the mobile device 20. Alternatively, the calculation module is placed inside a remote computer in communication with the photorefraction module 10. The calculation module generates a set of simulated images based on the data of the light sources used, the position of the photorefraction module 10 relatively to the eye 2 of the individual, and on the ophthalmic refraction data of the eye 2.

Figure 4:
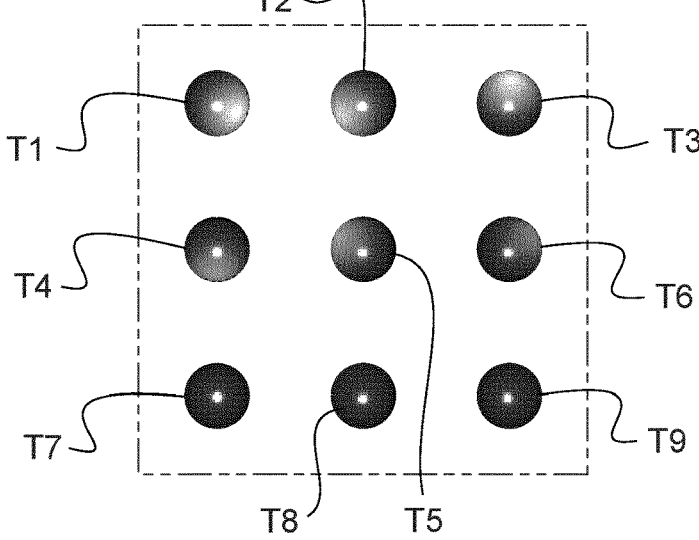
FIG. 4 illustrates a set of 9 acquired eccentric photorefraction images of an eye of an individual using the system and method according to the invention.

In a preliminary step, the system 50 is used to acquire a set of N eccentric photorefraction images as shown on FIG. 4. For example, the system uses M=9 light sources as detailed in relation with FIG. 2. In an embodiment, the system 50 is configured to capture one image for each eccentric flash which are lit sequentially. For example, the light source 16-A1 emits a flash while all the other light sources are off and the system 50 captures a first eccentric photorefraction image T1 of the pupil of the eye 2. Next, the light source 16-A2 emits a flash while all the other light sources are off and the system 50 captures a second eccentric photorefraction image T2 of the pupil. Repeating this flash and acquisition, the system 50 acquires N=9 eccentric photorefraction image T1, T2, . . . T9 of the pupil of the eye 2, each image corresponding to a single light source of determined position. Then, the system stores in memory the set of 9 acquired eccentric photorefraction images T1-T9 of the pupil of the eye 2. For 12 leds, capturing a set of 12 acquired eccentric photorefraction image T1-T12 takes less than 0.5 second. This short acquisition time enables to maintain a constant pupil diameter of the eye 2, and reduces the risk that the eye accommodation changes between the different acquisitions. Increasing the number of light sources enables increasing the range of refraction measurements. Advantageously, the system 50 may be configured to acquire images of both eyes of the subject at the same time, thus capturing a distinct set of N acquired eccentric photorefraction images for each eye. Each image stored is associated with a light source of determined position relatively to the subject's eye 2 and to the camera 30.

The system 50 is easy to use. The acquisition of a set of images is as simple as taking a picture, as shown in FIG. 3.

Then, as illustrated on FIG. 5, the method is based on comparing a set of N simulated images to the set of N acquired eccentric photorefraction images of the eye, and on adjusting a combination of parameters so that the set of simulated images matches the set of acquired eccentric photorefraction images. More precisely, the method comprises an initialization step 100, for initializing parameters such as sphere, cylinder and axis values for the eye 2; a step 110 of setting values for parameters (parameters related to the eye sought including at least sphere, cylinder and axis, and optionally high order aberrations or HOA, hardware related parameters and measurement parameters, such as measuring distance); a step 120 of generating a set of simulated images based on the values for parameters set at step 110; a step 130 of comparing the set of simulated images with a set of target images, i.e. to the set of acquired eccentric photorefraction images of the eye sought; and a step 140 of optimizing or minimizing an estimator of a difference between the set of simulated images with the set of target images. The steps 110, 120, 130 and 140 are iterated until a minimum is found.

The method illustrated on FIG. 5, like any optimization algorithm or minimization algorithm, needs a starting point, or an initialization step 100.

When using an optimization algorithm, one seeks to optimise the merit function of the algorithm. In general, the merit function of this algorithm is minimized.

When using a minimization algorithm, one seeks to minimize the estimator of a difference between the set of simulated images with the set of target images.

The initialization step 100 may rely on data from a previous prescription of the subject, enabling to initialize the sphere, cylinder and axis values for the eye sought.

Alternatively, the initialization step 100 is based on a classical known method such as meridians, described in relation with FIG. 6. Here are the different steps of the treatment. The aberrations of an eye can be approached at first order by a component of sphere (S), cylinder (C) and axis (A) of this cylinder which can be represented according to this diagram on FIG. 6. The dots 16-A, 16-B, 16-C correspond to infrared LEDs with the highest eccentricity on each meridian, respectively $X_A$, $X_B$ and $X_C$. At least three meridians are required for determining S, C and A. Therefore, for each meridian, we look in the corresponding image $T_j$ for a pupil diameter as well as rising or falling fronts, i.e. abrupt transitions between a high grey level and a low grey level, thus translating the typical dark crescent in photorefraction measurement.

FIG. 7 illustrates an eccentric photorefraction image acquired using a single light source placed along meridian $X_A$ for example. The straight line represents the meridian $X_A$. The circle 42 represents a simulation of the pupil of the eye, and enables to determine the pupil diameter $D_P$. Image processing enables to identify the dark crescent 41 and the bright crescent 51. Curved line 43 represents a theoretical crescent based on a pure sphere S. Curved line 44 represents a theoretical crescent based on a combined sphere S and cylinder C values. The intersection between curved lines 43 and 44 with the meridian enables to determine the size $D_{CR}$ of the dark crescent 41. Alternatively, the size of the bright crescent 51 can also be used. The optical power along the meridian considered derives from the following formula [1]:

$$P_{meridian} = \frac{1}{DistZ} \cdot \left(1 + \frac{e}{D_{CR}}\right)$$

where $P_{meridian}$ represents the ophthalmic power along this meridian, DistZ the distance in meters at which the measurement is made, that is the distance between the subject 1 and the camera 30, e the eccentricity in mm and $D_{CR}$ the length of the dark crescent.

Thus, the optical power is measured for each of the three meridians, respectively $X_A$, $X_B$ and $X_C$. This enables to determine at least three powers from three different angles $\theta$ as illustrated on FIG. 8. In this example, meridian $X_A$ is at an angle of 30 degrees, meridian $X_B$ is at an angle of 150 degrees and meridian $X_C$ is at an angle of 270 degrees. The sphere (S), cylinder (C) and Axis (A) data are derived from the following formula [2]:

$$P(\theta) = S + C \cdot \sin^2(\theta - A)$$

Formula [1] is theoretically limited to an eye whose refractive error is a pure sphere. Nevertheless, this method gives an exploitable starting point for the following minimization algorithm, by providing initial values for the parameters of the simulator.

The step 120 of generating a set of simulated images aims at generating images similar to the ones provided by the camera. This step starts with the initial values for parameters derived from previous step 110.

To run step 120, the processor uses a simulation model. For example, the simulation model is based on a geometrical-optical model of light intensity distribution. For example, the publications R. Kusel, U. Oechsner, W. Wesemann, S. Russlies, E. M. Irmer, and B. Rassow, "Light-intensity distribution in eccentric photorefraction crescents," J. Opt. Soc. Am. A 15, 1500-1511 (1998) and A. Roorda, M. C. W. Campbell, and W. R. Bobier, "Geometrical theory to predict eccentric photorefraction intensity profiles in the human eye," J. Opt. Soc. Am. A 12, 1647-1656 (1995) describe such geometrical-optical models. Alternatively, the simulation model is based on a ray-tracing model, for example based on Zemax optical design software, as detailed in Y-L. Chen, B. Tan, and J. W. L. Lewis, "Simulation of eccentric photorefraction images," Optics Express 11, 1628-1642 (2003). Nevertheless, the simulation model can be implemented based on another model among many models, and not only based on geometrical-optical or ray-tracing models.

The simulation model takes into account different types of parameters. More precisely, the parameters belong to the following categories: 1—ophthalmic parameters related to the eye sought, 2—hardware related parameters and 3—parameters linked to the measurement protocol.

More precisely, the ophthalmic parameters related to the eye sought comprise at least one of the following parameters:

Pupil radius (R),
Spherical power (S) which is a low order aberration (LOA),
Cylindrical power (C) which is a LOA,
Cylinder axis (A) which is a LOA,
Higher order aberrations (HOA), represented by Zernike coefficients A6w to A14w,
Pupillary half deviation,
Direction of gaze,
"Red Reflex" (RR) which represents the luminous offset due to multiple diffuse reflections on the retina,
Stiles-Crawford effect (SC), and/or
the Purkinje reflections of the eye.

The hardware related parameters may comprise at least one of the following parameters:

Position and apparent size of the light sources, for example LEDs,
LED wavelength,
Light power of the light sources, for example LEDs, represented by G and R matrices for all the light sources,
the relative brightness of the different light sources,
Camera sensor gain, and optionally camera noise,
the exposure parameters of the camera,
Position and size of apertures of the optical system of the camera, among which the entrance pupil of the camera, (dxCam, dyCam),
Focal length of the optical system of the camera,
Pixel size, dynamic
The point spread function of the optical system of the camera.

The parameters linked to the measurement protocol may comprise at least one of the following parameters:

Measuring distance,
Central position of the eye(s) in the image.

The positions of the set of M light sources are critical parameters for the simulation step 120 and for the minimization or optimization step 140. However, the positions of the set of M light sources are fixed and are not optimized in step 140.

According to the simulation model used, the combination of all these parameters enables to generate one image per light source (here per led). In the example illustrated on FIG. 10, the simulation model generates 9 images 0S1 to 0S9 at this initial step of the simulation.

FIG. 10 shows the set of simulated images 0S1, 0S2, . . . 0S9 obtained with the initial values of the parameters displayed on the left. FIG. 10 shows as well the set of target images T1, T2, . . . T9. The target images T1, T2, . . . T9 correspond to the acquired eccentric photorefraction images captured and stored in memory as detailed in relation with FIG. 4. More precisely, the target image corresponds to the central part, inside the pupil, of the acquired eccentric photorefraction image, the area around the pupil being set to a black background. FIG. 10 corresponds to iteration n° 0, i.e., the parameters are at nominal values, 0 for the HOA, identical light power (G and R matrices) for all the leds. The sphere, cylinder and axis values are filled in using the meridians method for example. The pupil radius R value is also filled in by measuring by image processing methods the best circle with respect to the gradients present in the image and representing the pupil edge.

The calculation module computes the difference between each of the simulated image 0S1, 0S2, . . . 0S9 at iteration n°0 and each of the corresponding target image T1, T2, . . . T9. FIG. 10 also shows the resulting differential images 0D1, 0D2, . . . 0D9 with the numerical difference corresponding to each differential image. The differential image is here calculated based on a pixel-by-pixel intensity difference of the area inside the image of the pupil. An estimator, denoted E, of the difference between the two sets of images is calculated based on the following formula $$E = \sum_{k=0}^{k=N} \sum_{i,j=0}^{nb\ pixels} (PixSimulated(i, j) - PixReal(i, j))$$

In the example of FIG. 10, the estimator of the difference between the set of 9 simulated image 0S1, 0S2, . . . 0S9 and the set of 9 target image T1, T2, . . . T9 is computed as the sum of the 9 numerical differences computed for each differential image. In the example of FIG. 10, the value of the overall estimator E0 at iteration n°0 is estimated to 210.810 (in arbitrary unit or a.u.).

Alternatively, the acquired images and the simulated images are preprocessed, e.g. by Fourier filter or other filters, and then compared with each other.

Next, at iteration n°1, the minimization algorithm starts a backpropagation loop. Indeed, the input parameters of the model need to be adjusted in order to minimize the value of the estimator. For that purpose, different minimization methods are available among: methods without gradient computation such as the simplex method or the Nelder-Mead method, to name a few; methods with gradient computation such as the Levenberg Marquardt method. In the following example we use the Levenberg Marquardt method. The minimization method is a stand alone algorithm, which can be used as a black box.

For each input parameter, the calculation module computes a gradient, i.e. the local derivative at that point. The gradient for each parameter then enables to calculate a displacement vector for each parameter. Thus, at step 140, the minimization algorithm adjusts the values of the set of input parameters used by the simulation model, such as the ophthalmic parameters, hardware parameters and/or parameters linked to the measurement protocol. FIG. 11 illustrates the results of iteration step n°1 for the same set of target images T1 to T9. The adjusted values of the input parameter are displayed on the left side of FIG. 11. FIG. 11 shows the set of simulated images 1S1, 1S2, . . . 199 obtained with the values of the parameters adjusted at iteration n°1. The calculation module computes the difference between each of the simulated image 1S1, 1S2, . . . 199 at iteration n°1 and each of the corresponding target image T1, T2, . . . T9. FIG. 11 also shows the resulting differential images 1D1, 1D2, . . . 1D9 with the numerical difference corresponding to each differential image. In the example of FIG. 11, the value of the overall estimator E1 at iteration n°1 is estimated to 70.655 (a.u.). Thus, a fast decrease of the overall estimator of the difference between the set of simulated images and the set of target images is observed from the first iteration.

By iterating this procedure, a number of times, until estimator E no longer converges, the calculation unit reaches a local minimum.

The minimization algorithm is iterated until a stopping condition is reached. Each minimization algorithm may use different stopping criteria. For example, a stopping condition may be when the estimator is smaller than a predetermined value. Another stopping condition is based on the residual difference between S, C, A values, for example if the difference is lower than 0.01 diopter between two successive iterations, the minimization stops. Another stopping condition may be a maximum number of 20 iterations.

Pursuing with the same example, as FIGS. 10 and 11, the minimization algorithm is iterated until iteration N°16, where the minimization algorithm is stopped. FIG. 12 illustrates the results of iteration step n°16 for the same set of target images T1 to T9. The adjusted values of the input parameter are displayed on the left side of FIG. 12. FIG. 12 shows the set of simulated images 16S1, 16S2, . . . 16S9 obtained with the values of the parameters adjusted at iteration n°16. The calculation module computes the difference between each of the simulated image 16S1, 16S2, . . . 16S9 at iteration n°16 and each of the corresponding target image T1, T2, . . . T9. FIG. 12 also shows the resulting differential images 16D1, 16D2, . . . 16D9 with the numerical difference corresponding to each differential image. In the example of FIG. 12, the value of the overall estimator E16 at iteration n°16 is estimated to 4.176 (a.u.). Thus, a fast decrease of the overall estimator of the difference between the set of simulated images and the set of target images is observed after 16 iterations. The method enables an accurate estimation of the ophthalmic parameters which are close to the target values for low order aberrations such as sphere, cylinder and axis, and also for the Zernicke coefficients of the high order aberrations.

The computing time to obtain these results is about few seconds. The method described herein enables to obtain accurate results for sphere, cylinder and axis, and further enables to estimate high order aberrations without requiring bulky instruments.

The example detailed above is based on acquiring each image with a single light source on, while all other light sources are off. Alternatively, two light sources may be used simultaneously for acquiring each eccentric photorefraction image of the pupil of the eye considered. For example, FIG. 9 illustrates an image captured with 2 LEDs lit on simultaneously. The two LEDs are arranged along two different meridians to avoid superposition of two crescents. We observe a first bright crescent 51 generated by a first LED placed along meridian $X_A$ and a second bright crescent 52 generated by a second LED placed along meridian $X_B$. The first bright crescent 51, respectively second bright crescent 52, is delimited by the abrupt transitions curve 41, respectively 42, between a high grey level and a low grey level in the image. Thus, it is possible to determine the size of two dark crescent from a single eccentric photorefraction image capture.

More generally, a set of N images are taken with two LEDs lit on simultaneously to generate 2 crescents in the pupil. Preferable the two light sources are arranged on 2 different meridians. For example, a first image Im1 is captured using two LEDs n11, n12; a second image Im2 is captured using two other LEDs n21, n22; and a third image Im3 is captured using two other LEDs n31, n32.

The simulation step is adapted by generating a set of N corresponding images with the same configuration Im1$s$ (LED n11, n12); Im2$s$ (LED n21, n22); Im3$s$ (LED n31, n32) . . . for a given set of parameters (Sph, Cyl, axis . . . ).

The same principle of optimisation, comparison of Imj/Imjs is applied during minimization steps.

According to another embodiment, two or more LEDs from the same meridian are lit on simultaneously. In this case, the captured image is processed to determine the gradient of light in the light distribution along this meridian, instead of determining the precise shape of the crescents.

The method described above is implemented in a computer program. It can also be implemented as a smartphone application to be loaded in a smartphone equipped with an add-on photorefraction module 10, as described above.

The combination of a photorefraction module 10 for capturing a set of eccentric photorefraction images and the corresponding application for simulation and minimization is easily adapted for any customer in the world owning a smartphone desiring a low cost tool providing quickly with a good starting point before proceeding with subjective refraction.

The invention of the present disclosure enables to equip population in rural areas and/or in emerging markets. The invention of the present disclosure enables non-professionals optometrists such as teachers, school nurses, volunteers in NGOs to realize mass screening in order to detect ametropia, worldwide in schools, governmental programs.

The system and method disclosed herein can also be embedded as a technical brick in another medical equipment for eye analysis, e.g. for subjective refraction measurement.

Although representative processes and systems have been described in detail herein, those skilled in the art will recognize that various substitutions and modifications may be made without departing from the scope of what is described and defined by the appended claims.

The invention claimed is:

1. A method for estimating refraction of an eye of an individual, the method comprising the following steps:

a) providing a set of N acquired eccentric photorefraction images of the eye, where N is an integer higher than or equal to one;

b) initializing values for a set of parameters including at least sphere;

c) providing a set of N simulated eccentric photorefraction images using a simulation model according to the values of the set of parameters;

d) determining an estimator of a difference between the set of N acquired eccentric photorefraction images and the set of N simulated eccentric photorefraction images;

e) performing an optimization using an optimization algorithm so as to optimize said estimator by adjusting values for the set of parameters and iterating steps c) and d); and f) deducing an estimation of at least one refraction parameter of the eye from the adjusted values for the set of parameters, wherein step a) includes the following steps g) to i), and each step c) includes the following step j):

g) placing a system comprising an image capturing device having an aperture and a plurality of M light sources in front of the eye, where M is an integer higher than or equal to two, the plurality of M light sources being arranged eccentrically around the aperture of the image capturing device at determined positions along at least two directions transverse to an optical axis of the image capturing device, each light source of the M light sources being adapted and configured to illuminate the eye with a light pulse;

h) illuminating the eye using each light source of the plurality of M light sources;

i) recording the set of N acquired eccentric photorefraction images of the eye using the image capturing device, where N is lower than or equal to M, each image of the set of N acquired eccentric photorefraction images representing the eye illuminated by the light pulse of at least one light source of the plurality of M light sources; and j) generating the set of N simulated eccentric photorefraction images using the simulation model according to the values of the set of parameters.

2. The method according to claim 1, wherein the step b) comprises selecting a set of three acquired eccentric photorefraction images from the set of N acquired eccentric photorefraction images, the set of three acquired eccentric photorefraction images being recorded using three light sources arranged along three directions transverse to the optical axis of the image capturing device; processing each of the three acquired eccentric photorefraction images so as to determine a dark crescent size and tilt angle, and deducing therefrom three ophthalmic power values for the three directions.

3. The method according to claim 2, wherein M is equal to N and the step h) comprises illuminating the eye using sequentially each light source of the plurality of M light sources, and wherein the step i) comprises acquiring each image of the set of N eccentric photorefraction images when the eye is illuminated by the light pulse of one light source of the plurality of M light sources.

4. The method according to claim 2, wherein N is lower than M and the step h) comprises a step of illuminating the eye using simultaneously with two light sources of the plurality of M light sources, and wherein the step i) comprises a step of acquiring one image of the set of N eccentric photorefraction images when the eye is illuminated by the light pulse of two light sources.

5. The method according to claim 2, wherein the simulation model is based on a geometrical-optical model of light intensity distribution or on a ray-tracing model.

6. The method according to claim 2, wherein the simulation model further depends on hardware parameters such as power of each light source, on ophthalmic parameters such as corneal reflection and/or on operational parameters such as position of the image capturing device relatively to the eye.

7. The method according to claim 1, wherein M is equal to N and the step h) comprises illuminating the eye using sequentially each light source of the plurality of M light sources, and wherein the step i) comprises acquiring each image of the set of N eccentric photorefraction images when the eye is illuminated by the light pulse of one light source of the plurality of M light sources.

8. The method according to claim 1, wherein N is lower than M and the step h) comprises a step of illuminating the eye using simultaneously with two light sources of the plurality of M light sources, and wherein the step i) comprises a step of acquiring one image of the set of N eccentric photorefraction images when the eye is illuminated by the light pulse of two light sources.

9. The method according to claim 1, wherein said simulation model is based on a geometrical-optical model of light intensity distribution or on a ray-tracing model.

10. The method according to claim 1, wherein the simulation model further depends on hardware parameters such as power of each light source, on ophthalmic parameters such as corneal reflection and/or on operational parameters such as position of the image capturing device relatively to the eye.

11. The method according to claim 1, wherein the estimator is based on pixel-by-pixel difference between the set of N acquired eccentric photorefraction images and the set of N simulated eccentric photorefraction images, or wherein the estimator is based on comparing a preprocessed set of N acquired eccentric photorefraction images and a preprocessed set of N simulated eccentric photorefraction images.

12. The method according to claim 1, wherein the optimization algorithm or the minimization algorithm is based on a method without gradient computation, such as simplex or Nelder-Mead, or on a method with gradient computation, such as Levenberg-Marquardt.

13. The method according to claim 1, further comprising determining a distance between the image capturing device and the eye and/or an orientation of the image capturing device relatively to the eye.

14. The method according to claim 1, wherein the set of parameters further comprises at least one other parameter of the eye among: cylinder, axis, pupil diameter, higher order aberrations, half interpupillary distance, direction of gaze, amount of red reflex, and Stiles-Crawford parameter.

15

15. A system for estimating refraction of an eye of an individual, the system being adapted to communicate with a mobile device or with a remote computer, the system comprising:

an image capturing device and a plurality of M light sources, where M is an integer higher than or equal to two, the plurality of M light sources being arranged eccentrically around the image capturing device at determined positions along at least two directions transverse to an optical axis of the image capturing device, the system being adapted and configured to illuminate the eye with a light pulse using each light source of the plurality of M light sources, and the image capturing device being configured to record a set of N acquired eccentric photorefraction images of the eye, where N is an integer lower than or equal to M, each image of the set of N acquired eccentric photorefraction images representing the eye illuminated by the light pulse of at least one light source of the plurality of M light sources; and a calculation module comprising a memory and a processor arranged to execute a program instructions stored in the memory to:

k) initialize values for a set of parameters including at least sphere;

l) Generate a set of N simulated eccentric photorefraction images using a simulation model based on the values of the set of parameters;

m) calculate an estimator of a difference between the set of N acquired eccentric photorefraction images and the set of N simulated eccentric photorefraction images;

n) use a minimization algorithm so as to minimize said estimator by adjusting values for the set of parameters and iterating steps l) and m); and o) deduce an estimation of at least one refraction parameter of the eye from the adjusted values for the set of parameters.

16

16. The system according to claim 15, wherein the image capturing device and the plurality of M light sources are mounted on an accessory removably attached to the mobile device.

17. The system according to claim 16, wherein the calculation module is included in the mobile device or in the remote computer.

18. The system according to claim 15, wherein the calculation module is included in the mobile device or in the remote computer.

19. A non-transitory computer-readable storage medium including one or more stored sequences of instructions that are accessible to a processor, and which, when executed by the processor, causes the processor to carry out at least the following steps to:

p) provide a set of N acquired eccentric photorefraction images, wherein each image of the set of N acquired eccentric photorefraction images represents an eye illuminated by a light pulse of at least one light source of a plurality of M light sources arranged eccentrically around an image capturing device at determined positions along at least two directions transverse to an optical axis of the image capturing device, where M is an integer higher than or equal to two, and N is an integer lower than or equal to M;

q) initialize values for a set of parameters including at least sphere;

r) generate a set of N simulated eccentric photorefraction images using a simulation model based on the values of the set of parameters;

s) determine an estimator of a difference between the set of N acquired eccentric photorefraction images and the set of N simulated eccentric photorefraction images;

t) use an optimization algorithm so as to optimize said estimator by adjusting values for the set of parameters and iterating steps r) and s); and u) deduce an estimation of at least one refraction parameter of the eye from the adjusted values for the set of parameters.

\* \* \* \* \*